United States Patent [19]

Milligan et al.

[11] Patent Number: 4,533,763

[45] Date of Patent: Aug. 6, 1985

[54] HYDROXY AROMATIC COMPOUNDS FROM ALKALI METAL HYDROXIDE AND MONONUCLEAR AROMATIC COMPOUND

[75] Inventors: Barton Milligan, Coplay; George B. DeLaMater, Macungie, both of Pa.

[73] Assignee: Air Products and Chemicals, Inc., Allentown, Pa.

[21] Appl. No.: 561,615

[22] Filed: Dec. 14, 1983

[51] Int. Cl.³ .............................................. C07C 39/02
[52] U.S. Cl. ..................................... 568/716; 568/780
[58] Field of Search ........................ 568/716, 780, 806

[56] References Cited

U.S. PATENT DOCUMENTS

| | | | |
|---|---|---|---|
| 2,119,213 | 5/1938 | Kasehagen et al. | 568/716 |
| 2,736,752 | 2/1956 | Hoffman et al. | 568/763 |
| 3,230,266 | 12/1983 | Baldwin et al. | 568/763 |
| 3,520,940 | 7/1970 | Smith | 568/763 |
| 4,172,960 | 10/1979 | Baldwin et al. | 568/763 |

FOREIGN PATENT DOCUMENTS 2362694 6/1974 Fed. Rep. of Germany ...... 568/763

*Primary Examiner*—Werren B. Lone
*Attorney, Agent, or Firm*—Russell L. Brewer; James C. Simmons; E. Eugene Innis

[57] ABSTRACT

This invention pertains to a process for preparing hydroxy mononuclear aromatic compounds by reacting an alkali metal hydroxide with a mononuclear aromatic compound, e.g., benzene, xylene or toluene. The reaction is carried out in the presence of a metallic hydrogenation catalyst, suitably copper, nickel, rhodium or cobalt, the metal being present in an amount sufficient for catalyzing the reaction. The hydroxy mononuclear aromatic compound is then formed by adding a protonating agent to the resulting reaction product, with the protonating agent liberating the hydroxy compound from the salt.

7 Claims, No Drawings

HYDROXY AROMATIC COMPOUNDS FROM ALKALI METAL HYDROXIDE AND MONONUCLEAR AROMATIC COMPOUND

TECHNICAL FIELD

This invention pertains to the manufacture of hydroxy aromatic compounds.

DESCRIPTION OF THE PRIOR ART

The production of hydroxy mononuclear aromatic compounds has been under study for decades. One technique has been to directly oxidize a mononuclear aromatic compound by reacting it with oxygen and this has been done with benzene and toluene. As is known, though, phenol is more easily oxidized than benzene thus the oxidation approach has not been successful from a commercial point of view. Toluene can be oxidized to form phenol, but it also results in by-product formaldehyde. This process also has not been successful from a commercial point of view.

Generally the standard commercial technique for producing the hydroxy compositions has been to react a halogenated aromatic or sulfonated aromatic with a hydroxyl providing reagent. For example, phenol is produced by reacting chlorobenzene with caustic soda at high temperature and pressure and then protonating the salt with a mineral acid. Another commercial technique, which is referred to as the alkali fusion of sulfonate, involves the conversion of benzene sulfonic acid to phenol.

SUMMARY OF THE INVENTION

This invention relates to a process for forming a hydroxy mononuclear aromatic compound by directly hydroxylating the mononuclear aromatic compound via nucleophilic substitution of the hydrogen atom on the aromatic ring. The direct hydroxylation is carried out by reacting a mononuclear aromatic compound with an alkali metal hydroxide in the presence of a metallic hydrogenation catalyst, the catalyst being present in an amount sufficient for catalyzing the reaction under the conditions utilized. The hydroxy composition then is liberated from the reaction product by adding a protonating agent such as a mineral acid.

Some of the advantages of the process are: it provides a direct method for preparing hydroxy aromatic composition, since the process involves direct nucleophilic displacement of a hydrogen atom as opposed to a nucleophilic displacement of groups such as halogen, nitrogen, and sulfonic acid; it offers efficiency in terms of raw materials; and it is energy efficient.

DETAILED DESCRIPTION OF THE INVENTION

A procedure has been developed which permits the direct substitution of a hydroxy group for the hydrogen atom on an aromatic compound as compared to the usual nucleophilic substitution of the hydroxy group for a halogen atom, sulfonate, or sulfinic group from the aromatic ring as performed by the prior art. In accordance with this invention, hydroxy mononuclear aromatic compounds are produced by effecting a catalytic reaction between a mononuclear aromatic composition and an alkali metal hydroxide. A catalyst must be used, since an alkali metal hydroxide and mononuclear aromatic composition, by themselves, are unreactive, and this unreactivity has been observed in the art. Examples of mononuclear aromatic compounds suited for practicing invention include benzene, toluene, xylene and cumene.

The hydroxyl functionality is supplied to the mononuclear aromatic compounds via an alkali metal hydroxide, which includes a lithium hydroxide, potassium hydroxide and sodium hydroxide. These metal hydroxides are sufficiently reactive to effect nucleophilic substitution of the hydrogen atom on the aromatic ring. Other hydroxides such as ammonium hydroxide and the alkaline earth metal hydroxides are not sufficiently reactive.

In order to effect reaction between the alkali metal hydroxide and mononuclear aromatic compound, a catalytic material must be present in the reaction system in an amount sufficient to catalyze the formation of the reaction product. Although a specific analysis of the composition of the reaction product has not been made at this time, it is believed that the reaction product is an alkali metal salt of a hydroxy aromatic. This belief is based partly on the fact that on the addition of a protonating agent to the reaction product, the hydroxy composition is liberated. Catalysts, suitable for effecting the reaction are hydrogenation catalyst such as copper, nickel, cobalt, and rhodium. As with conventional hydrogenation catalysts, these hydrogenation metals may be carried upon a support. However, the support should be stable under the reaction conditions. The metal catalyst used in the reaction system is provided in the amount sufficient to catalyze a reaction in the conditions set forth. Generally, this amount is from 01.–5% by weight of the alkali metal hydroxide.

The alkali metal hydroxide is incorporated into the reaction medium in at least a stoichiometric quantity for effecting nucleophilic displacement of the hydrogen ion with the group. Generally, quantities from one to five moles alkali metal hydroxide based on one mole quantity of mononuclear aromatic compound are utilized.

The temperature used in carrying out the reaction is that temperature necessary to effect the formation of the reaction product, which is generally from 200° to 300° C. The pressure utilized for the reaction is generally dictated by the vapor pressure of the organic reactant. Higher pressures do not significantly enhance the reaction.

After the initial reaction between the alkali metal hydroxide and mononuclear aromatic compound, the reaction product is contacted with a protonating agent to liberate the hydroxyl group. Typical protonating agents suited for converting the reaction product to the hydroxy mononuclear aromatic composition include aqueous mineral acids, such as sulfuric or hydrochloric acid. The protonating agent is added in an amount sufficient to convert the reaction product to the hydroxy composition. Typically, from about 1–1.5 moles protonating agent per mole of total base alkali metal hydroxide present are utilized. Liberation of the hydroxy group is readily effected at temperatures from 10° to 50° C. and atmospheric pressure.

In many instances it is preferable to separate the reaction product, i.e., the salt from the reaction medium prior to adding the protonating agent. This separation is desirable since the system would inherently contain large amounts of alkali metal hydroxide, which must be neutralized before the salt can be protonated. To avoid neutralizing all of the excess alkali metal hydroxide, it is necessary to convert the reaction product to a water insoluble, organic soluble system which then can be separated from the reaction mixture by addition of the protonating agent. Then, when the protonating agent is added, the product returns to an aqueous phase. Ion pair extraction is one technique which is well suited to the production of the hydroxy compounds. Ion pair extraction is effected by reacting tetrabutyl ammonium ion as the extractant and chlorobenzene or anisole as a solvent.

The following examples are provided to illustrate various embodiments of the invention.

EXAMPLES 1-20

A series of runs were carried out in a 300 cc high pressure reactor manufactured by Autoclave Engineers. It was equipped with a Magnedrive stirrer fitted with a copper insert to prevent corrosion of the stainless steel body.

Initially a charge of benzene or toluene, either solid sodium hydroxide or in solution form, and wet catalyst were added to the copper insert contained in the reactor body. The reactor was pressure checked with nitrogen at 2,000 psig and then vented to atmospheric pressure. An initial pressure in a range of 250–1,200 psig was then applied to the reactor as determined by a back pressure valve setting. The reactor was then filled with benzene from a reservoir by means of a pump.

The reaction was allowed to proceed at the reaction temperature for several hours e.g., 10–30 hours at which time the reaction was deemed complete. The reaction mixture was cooled, contacted with water and allowed to separate. The aqueous layer then was neutralized with sulfuric acid and the aqueous layer separated from the organic layer and extracted three times with ether.

Analysis of the organic phase, including all extracts, was made with a Perkin-Elmer Sigma I gas chromtograph using flame ionization detector and a Hewlett Packard 25 meter×0.2 millimeter fused silica capillary column with Carbowax 20M stationary phase. The column was an isothermal column maintained at temperature of 70° F. for 5 minutes, programmed at 20° F. per minute to 150° F. and held for three minutes. The injector temperature was 250° C. and the detector temperature was 275° C. Other conditions were split injection at 20 psig backpressure, 60 cc helium per minute and a 1 microliter sample size.

Examples 1–4 are more particularly described below.

EXAMPLE 1

Into the copper lined autoclave were charged 16 parts by weight of benzene and 80 parts of solid sodium hydroxide. Then 1 part by weight of Raney nickel catalyst (designated #28 by W. R. Grace Co.) was added. The autoclave was sealed, purged with nitrogen and heated to 325° C. for 19 hours. The reaction mixture was removed and added to water, which was then neutralized with sulfuric acid. The benzene layer was separated and the aqueous layer was extracted three times with ether. Gas chromatography of the combined extracts showed that 7 micrograms of phenol had been formed.

EXAMPLE 2

To allow for removal of any hydrogen gas formed, the procedure of Example 1 was modified to remove benzene continuously from the reactor by venting it to atmospheric pressure and then returning it to the autoclave with a small high pressure pump. At the end of the run at 315° C., the yield of phenol by gas chromatography showed that it had been formed at a rate of 20 micrograms per hour (389 micrograms total).

EXAMPLE 3

The procedure of Example 2 was repeated except that 50 weight parts of 50% aqueous sodium hydroxide was used in place of solid sodium hydroxide and the temperature was 290° C. The tubes used to remove liquid from the autoclave to the external recirculation vessel were placed at the benzene-sodium hydroxide solution interface so that both phases were transferred. In this case 261 micrograms of phenol were formed for a yield of 0.0004% based on the benzene charged.

EXAMPLE 4

The procedure of Run 3 was repeated except that a cobalt catalyst was used. This catalyst was prepared by adding concentrated aqueous ammonia to a solution of cobalt (II) nitrate in water. The precipitate that formed was filtered, suspended in concentrated aqueous ammonia and then reduced in an autoclave with 500 psi of hydrogen gas at 225° C. At the end of the run at 300° C. analysis by gas chromatography showed that phenol had been formed at a rate of 330 micrograms per hour.

Table 1 provides information with respect to the conditions used for the reaction in Examples 5–20 including the catalyst and amount. Ni refers to nickel, Pd/C refers to a palladium metal supported on carbon, and Rh/C refers to rhodium on carbon.

TABLE I

| Example | Aromatic/g | Caustic/g | Reaction Time (hr) | Temp. °C. | Catalyst Level/g | Results & Comments |
|---|---|---|---|---|---|---|
| 5 | Benzene (40) | 50% NaOH (40) | 19 | 300 | Pd/C (5.3 g) wet | Trace phenol. |
| 6 | Benzene (10) | 50% NAOH (37) | 19 | 300 | Rh/C (5 g wet) | 0.006 g phenol 0.04% yield 279 microgram phenol/hr. |
| 7 | Toluene (10) | 50% NaOH (37) | 19 | 300 | Rh/C (5 g wet) | cresol (primarily m-) 0.89 mg phenol 0.15 mg - yield 0.04%. |
| 8 | Benzene (25) | $CH_3O$ Na (8) $CH_3OH$ (24) | 15 | 270 | Rh/C (8 g wet) | No anisole |
| 9 | Toluene (10 g) | NaOH (2.2) $H_2O$ (43) | 15 | 275 | Rh/C (10 g) + (pre-reduced) | phenol (32 micro mole) + m-cresol (46 micro mole) 0.07% yield |
| 10 | Toluene (10 g) | NaOH (2 g) $H_2O$ (43) | 15 | 275 | Rh/C (5 g) + (pre-reduced) | phenol + m-cresol 0.10% total yield |
| 11 | Toluene (10 g) | NaOH (2 g) $H_2O$ (38 g) | 15 | 275 | Rh/C (5 g) (wet) not pre-reduced | phenol + m-cresol + trace p-cresol Yield 0.07% |
| 12 | Toluene (10 g) | NaOH (0.48) $H_2O$ (43) | 15 | 275 | Rh/C (5 g) wet | phenol + m-cresol Yield 0.029% |

TABLE I-continued

| Example | Aromatic/g | Caustic/g | Reaction Time (hr) | Temp. °C. | Catalyst Level/g | Results & Comments |
|---------|------------|-----------|-------------------|-----------|------------------|--------------------|
| 13 | Toluene (10 g) | NaOH (2.1) H$_2$O (38) | 15 | 275 | Rh/C (5 g) wet | phenol + m-cresol Yield 0.08% |
| 14 | Toluene (10 g) | NaOH (2) H$_2$O (38) | 15 | 275 | Rh/C (5 g) wet | phenol + m-cresol Yield 0.06% possible traces o- & p-cresols |
| 15 | Toluene (10 g) | NaOH (2) H$_2$O (40) | 69 | 275 | Rh/C (5 g) wet | 0.14% phenol + m-cresol (trace o- & p-cresols) + benzoic acid (major acidic product) |
| 16 | Toluene (10 g) | NaOH (2.0 g) + Water (40 g) | 15 | 275 | None | Traces only of phenol & m-cresol |
| 17 | Toluene (10 g) | NaOH (2.0 g) + Water (40 g) | 15 | 275 | CoCO$_3$/CaCO$_3$ (1.2) | Yield phenol + m-cresol 0.016% |
| 18 | Toluene (10 g) | NaOH (2.0 g) + Water (38 g) | 15 | 275 | Raney Cu 2 g wet | Yield phenol + m-cresol 0.006% |
| 19 | Toluene (12 g) | NaOH (2.0 g) + Water (38 g) | 15 | 275 | Rh/C 5 g wet | Stirrer shaft removed 0.015% yield |
| 20 | Toluene (10 g) | NaOH (2.0 g) + Water (38 g) | 15 | 275 | Rh/C 5 g wet | No stirrer, higher variac setting for higher reflux traces only phenol & m-cresol |

What is claimed:

1. In a process for forming a mono hydroxy mononuclear aromatic compound by reacting a mononuclear aromatic compound with a hydroxyl providing agent under conditions effective for forming a hydroxy mononuclear aromatic compound, the improvement which comprises:

forming an intermediate reaction product of a benzene, toluene or xylene by effecting reaction between said benzene, toluene or xylene and an alkali metal hydroxide, said reaction carried out at a temperature from 200°–300° C. in the presence of a metallic hydrogenation catalyst, said catalyst being present in an amount effective for catalyzing the reaction between the alkali metal hydroxide and benzene, toluene or xylene; and adding an aqueous mineral acid to the intermediate reaction product in sufficient amount to liberate the hydroxy mononuclear aromatic compound.

2. The process of claim 1 wherein said alkali metal hydroxide is selected from the group consisting of sodium hydroxide, lithium hydroxide or potassium hydroxide.

3. The process of claim 2 wherein said metallic hydrogenation catalyst is selected from the group consisting of copper, nickel, rhodium and cobalt.

4. The process of claim 2 wherein said catalyst is present in proportion of from 0.1 to 5% by weight based upon said benzene, toluene or xylene.

5. The process of claim 1 which includes the additional step of converting the intermediate reaction product to a water insoluble, organic soluble component and separating the organic soluble material from the water soluble material prior to protonating the intermediate reaction product.

6. The process of claim 4 wherein said aqueous mineral acid is included in a proportion of 1–1.5 moles per mole of total alkali metal hydroxide present.

7. The process of claim 6 wherein said aqueous mineral acid is aqueous sulfuric of hydrochloric acid.

* * * * *